(12) United States Patent
Lampropoulos et al.

(10) Patent No.: US 6,533,757 B1
(45) Date of Patent: Mar. 18, 2003

(54) MONITORING AND DISPLAYING PRESSURIZATION DATA

(75) Inventors: Fred P. Lampropoulos, Sandy, UT (US); Steven R. Taylor, Salt Lake City, UT (US); Thomas D. Stout, Salt Lake City, UT (US); Blaine A. Johnson, Riverton, UT (US); Larry E. Roberts, American Fork, UT (US); Jerrold L. Foote, Kanab, UT (US); A. Tony Smith, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 287 days.

(21) Appl. No.: 09/589,992

(22) Filed: Jun. 8, 2000

(51) Int. Cl.$^7$ ............................................. A61M 37/00
(52) U.S. Cl. .................. 604/131; 604/920; 604/100.03; 604/96.01; 604/97.02; 604/98.01
(58) Field of Search ................................. 604/131, 920, 604/100.01, 100.02, 100.03, 96.01, 97.01, 97.02, 97.03, 98.01, 98.02, 99.01, 99.02, 99.03, 509

(56) References Cited

U.S. PATENT DOCUMENTS

| | | | |
|---|---|---|---|
| 5,259,838 A | * 11/1993 | Taylor et al. | ............ 604/97.03 |
| 5,300,027 A | 4/1994 | Foote et al. | ................ 604/100 |
| 5,449,344 A | * 9/1995 | Taylor et al. | ............ 604/97.03 |
| 5,453,091 A | * 9/1995 | Taylor et al. | .......... 604/100.03 |
| 5,458,571 A | * 10/1995 | Lampropoulos et al. | ..... 604/509 |
| 5,647,847 A | * 7/1997 | Lafontaine et al. | .... 604/100.03 |
| 6,190,354 B1 | * 2/2001 | Sell et al. | ................ 604/96.01 |

* cited by examiner

Primary Examiner—Teresa Walberg
Assistant Examiner—Fadi H. Dahbour
(74) Attorney, Agent, or Firm—Workman, Nydegger & Seeley

(57) ABSTRACT

Methods and systems for controlling and monitoring pressurization data. The methods and systems advance beyond the prior art in their ability to convey pressurization data unambiguously. The methods and systems include a novel combination of visual cues and control features to insure that pressurization data may be analyzed accurately. For example, the visual cues and control features include changing the background color of the display area and providing a pressurization arrow to indicate pressurization or depressurization; a time showing the elapsed time of pressurization or depressurization; a pressurization number indicating the number of pressurization cycles that have occurred; software keys for making configuration choices; and text and graphic display modes. A touch interface may be provide for user interaction. To insure accurate pressure measurements, at least one pressure reference standard may also be utilized.

61 Claims, 6 Drawing Sheets

Main Menu

- ~ History
- ~ Set Units

- ~ No Syringe Connected
  or
- ~ Syringe Connected and No Pressurization

- ~ Clear
- ~ Setup

- ~ Language
  - ~ Time
  - ~ Date
  - ~ High Trigger
  - ~ Low Trigger
  - ~ Printer
  - ~ Remote

- ~ No Syringe Connected

FIG. 3A

Setup Menu

Time
Date
High Trigger
Low Trigger
Printer
Remote

Press "OK" to enter the language selection menu.

OK

EXIT

FIG. 3B

MONITORING AND DISPLAYING PRESSURIZATION DATA

BACKGROUND OF THE INVENTION

1. The Field of the Invention

The present invention relates to methods and systems for controlling and monitoring pressurization data. More specifically, the methods and systems may be used to control and monitor the pressurization of a control syringe during certain medical procedures.

2. The Prior State of the Art

One of the most common medical procedures that requires precise measurement of pressurization data is balloon coronary angioplasty, more technically known as percutaneous transluminal coronary angioplasty ("PTCA"). PTCA was developed about twenty years ago as an alternative to existing techniques for treating coronary artery disease. Bypass surgery and drug therapy had been the principal treatment options of the day. However, bypass surgery is extremely traumatic on the patient and drug therapy attempts only to compensate for the effects of coronary artery disease as opposed to treating the disease itself. PTCA, in contrast, is a comparatively minor procedure directed at eliminating (rather than merely compensating for) the dangers posed by coronary artery disease. Notwithstanding the comparatively minor nature of PTCA procedures, strict control and monitoring of pressurization data is essential to the patient's safety.

A leading cause of death for many years, coronary artery disease is a narrowing or blockage ("stenosis") of the arteries that supply oxygen-rich blood to the heart. In coronary artery disease, the narrowing or blockage is caused by artherosclerosis, a buildup of waxy material (cholesterol and other fats) called plaque inside the artery walls. The waxy buildup reduces the amount of oxygenated blood that can flow to the heart through the coronary arteries. For many, this reduced blood supply results in a symptom of coronary artery disease called angina pectoris ("angina").

Angina is characterized by chest pain or pressure that may radiate to the arm or jaw, and is caused by insufficient oxygen being delivered to the heart muscle. At rest, the reduced flow of oxygenated blood caused by coronary artery disease may remain undetected, particularly in the early stages of the disease. However, under exertion or stress, the heart demands increasing amounts of oxygen to continue functioning properly. When the narrowed or obstructed coronary arteries prevent the heart from receiving the extra supply of oxygen-rich blood that is required to sustain a given heart rate, the resulting oxygen deficiency causes angina.

As noted earlier, up until the early seventies there were two basic ways to treat coronary artery blockages: drug therapy or coronary artery bypass surgery. Drug therapy involved administering various medications to decrease the work of the heart by slowing the heart rate, dilating the blood vessels, or lowering blood pressure. However, drug-based treatment did not restore normal supply of blood to the heart, the medicine simply alleviated the discomfort that may be associated with coronary artery disease. The underlying problem of reduced blood flow remained and continued to present a risk that at some point the blockage would become serious enough to require surgical intervention.

In coronary artery bypass surgery, a blood vessel from the chest or leg is grafted beyond the point of blockage so that blood flow detours around the blockage in order to reach the heart muscle. In some severe cases, multiple bypasses must be performed. As is well known, coronary artery bypass surgery is an expensive, high-risk procedure and often requires prolonged hospitalization and recovery periods.

PTCA, in contrast, is a much less traumatic procedure than coronary artery bypass surgery. PTCA procedures typically last about two hours and are performed under local anesthesia. Often, a patient can be walking and active in a matter of hours. Because PTCA is much less expensive and less traumatic than bypass surgery and yet in many cases effectively removes blockage, PTCA has experienced a dramatic increase in the number of procedures performed each year. For example, according to some reports, by 1987 some 200,000 patients suffering from coronary artery disease had been treated using PTCA. Significantly, as of 1987, approximately six million cases of coronary artery disease were reported in the United States alone. Therefore, PTCA may be expected to continue playing an important role in the treatment of coronary artery disease.

In performing PTCA, an introducer sheath is inserted through an incision made in the groin or in the artery of an arm. Through a catheter that is introduced through the sheath, an x-ray sensitive dye is injected into the coronary artery. The dye enables the doctor, through the use of real time x-ray techniques, to clearly view the arteries on a television monitor and to thereby locate the artery blockage. With the help of images from the x-ray monitor, a balloon-tipped catheter is fed over a guide wire and advanced through the artery to the point of the blockage.

The balloon catheter is advanced to the middle of the blockage site. This catheter, which is also filled with a radio-opaque fluid, is coupled at its other end to a control syringe being manipulated by a cardiologist. Once the balloon catheter is in place, the cardiologist uses the control syringe to inflate the balloon for time periods ranging from about 20 to 60 seconds. At the end of each time period, the cardiologist operates the control syringe to deflate the balloon. Typically, the inflation/deflation cycle is repeated several times to compress the plaque on the arterial wall. After the results are checked, the balloon catheter and guide wire are removed.

Even though PTCA is a much less traumatic procedure than coronary artery bypass surgery, exacting control with respect to inflation pressure and duration of the inflation periods is essential to the safety of the patient. When the balloon catheter is inflated so as to begin compressing the plaque, blood flow to that area of the heart is temporarily shut off. Depriving the heart muscle of its blood supply, even temporarily, creates the potential for initiating cardiac arrest. Accordingly, the attending cardiologist and other personnel must carefully control both the pressure exerted on the artery walls and the duration of the temporary blockage. The inflation pressure and duration for each inflation are based on the cardiologist's assessment of the patient's overall health and ability to withstand a temporary stoppage of blood flow to the heart.

In the past, PTCA syringe systems have used standard pressure gauges to sense and read the pressure of an inflated balloon catheter, with human observation of stop clocks and the like controlling the duration of each inflation. While these prior art techniques have been widely used with success, they introduce a serious risk of human error. The gauges used on such syringe systems are often awkward and difficult to read accurately, and are subject to malfunction. Thus, improper recording of inflation pressure and/or duration may occur.

To enhance the monitoring, display, and recording of pressurization data, U.S. Pat. No. 5,300,027 issued to Foote, et al. on Apr. 5, 1994 and entitled "SYSTEM AND METHOD FOR MONITORING AND DISPLAYING BALLOON CATHETER INFLATION AND DEFLATION DATA" (hereinafter "Foote"), which is incorporated herein by reference, introduces an electronic control system. The control system includes a monochromatic LED display showing the pressurization data (number, time, and pressure) for the current pressurization cycle.

At the time, Foote represented a vast improvement over the prior art. Nevertheless, continuously improving medical care requires constant innovation. In the case of monitoring and controlling pressurization data, there is an ongoing need to enhance the information that may be conveyed to a cardiologist and/or clinician. The systems and methods of the present invention offer novel solutions to providing medical professions with immediate access to information, helping insure the best possible healthcare for their patients.

SUMMARY OF THE INVENTION

The present invention is directed toward methods and systems for electronically tracking pressurization data. For example, the present invention includes an electronic controller for receiving, displaying, and storing pressurization data. The present invention combines novel control features and display elements for conveying pressurization data in ways that were previously unknown. A preferred embodiment of the present invention is designed for use in displaying, monitoring, and storing pressurization data during a balloon coronary angioplasty procedure for treating coronary artery disease. Throughout these balloon catheter procedures, it is imperative for the medical professional performing the surgery to have immediate access to clear and accurate pressurization data.

In this environment, the electronic controller receives pressurization data from a control syringe equipped with a transducer for converting pressure information to electrical signals that can be interpreted by the controller. Optionally, the electronic controller may be attached to a printer and may also act as host for a remote electronic controller. When connected to a remote electronic controller, the host functions and displays are duplicated in both controllers. However, a control syringe may be connected only to the host.

As described above, balloon catheter procedures for treating coronary artery disease involve the insertion of an inflatable balloon catheter into a narrowed or blocked area of the arteries supplying oxygenated blood to the heart muscle. Using a control syringe, a clinician treating coronary artery disease inflates the balloon to compress plaque that has been deposited within the artery walls and is restricting the flow of blood. Because the inflated balloon temporarily stops blood from flowing through the artery, it is vital for the physician to know how much pressure the balloon is exerting on the artery wall and how long the balloon has been inflated.

The principal danger of the procedure is that interrupting the flow of blood to the heart will cause the patient to experience a cardiac arrest. Therefore, the precise pressure and duration of each inflation must be based on an assessment of the patient's health and the patient's ability to withstand temporarily halting the flow of blood to an area of the heart. Because the consequences of over inflating or stopping blood flow for too long are grave, the capability to clearly and accurately track pressurization data is critical to appropriate patient care.

The present invention is an advancement over the prior art in its ability to convey pressurization data unambiguously. Specifically, the present invention provides a unique combination of visual cues and control features to insure accurate analysis of pressurization data. For example, the background color of the display area changes when pressurization data transitions from one pressurization state to another (e.g., from a state of depressurization to a state of pressurization). Each transition between pressurization states also starts a timer showing the elapsed time since the transition occurred. To insure a clear understanding of pressurization data, units of measure are included with the display of pressurization values.

Together with changes in background color, a pressurization arrow in the display area visually communicates whether pressurization values indicate a state of pressurization or a state of depressurization. Within the pressurization arrow, the electronic controller displays a count of the pressurization cycles (i.e., the number of times pressurization values have transitioned between a predefined sequence of pressurization states). The bottom of the display area includes software buttons that allow for altering the operation of the electronic controller, such as how the display is organized. Specifically, one of the software buttons toggles between a text display mode and a graphical display mode.

The display also includes a touch interface for all interaction with the electronic controller. Pressing the display area showing the units of measure toggles between the various options for pressure units. Likewise, the software buttons along the bottom of the display are also activated through the touch interface.

To insure accurate pressure measurements, the present invention may include at least one reference standard. The reference standard may be read at various times during operation of the electronic controller to verify that the controller measures the same pressure at a consistent value. Minor variations in reference standard measurements are accounted for by defining an appropriate tolerance value or range.

Notwithstanding that the foregoing summary and later detailed description refer to balloon catheter treatment of coronary artery disease, the present invention is in no way limited to use in those procedures or even limited to medical applications in general. The present invention integrates various display cues, setup parameters, and control features to provide novel methods and systems for tracking pressurization data. These methods and systems may improve healthcare or offer the benefits of clarity, accuracy, and convenience to any other field or application.

These and other objects, features, and advantages of the present invention will become more fully apparent from the following description and appended claims, or may be learned by practicing the invention as set forth below.

BRIEF DESCRIPTION OF THE DRAWINGS

A more extensive description of the present invention, including the above-recited features, advantages, and objects, will be rendered with reference to the specific embodiments that are illustrated in the appended drawings. Because these drawings depict only exemplary embodiments, the drawings should not be construed as imposing any limitation on the present invention's scope. As such, the present invention will be described and explained with additional specificity and detail through use of the accompanying drawings in which:

FIG. 3A shows the setup options available from the electronic controller's main menu;

FIG. 3B illustrates the entry of setup parameters;

DETAILED DESCRIPTION OF THE PREFERRED EMBODIMENTS

Figure 1A:
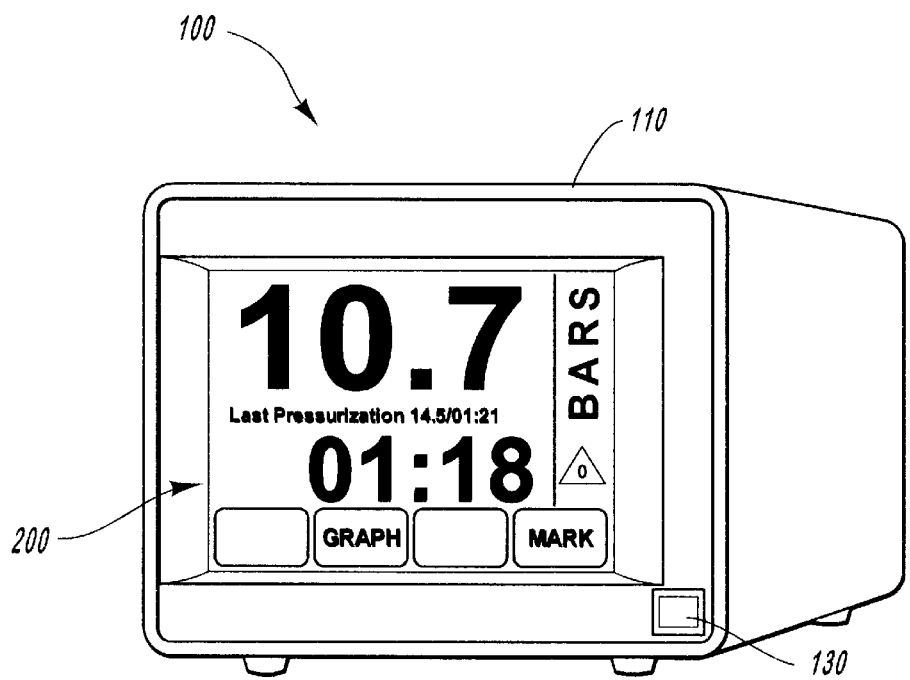
FIGS. 1A and 1B show a preferred embodiment of an electronic controller according to the present invention.

The invention is described below with reference to drawings. These drawings illustrate certain details of specific embodiments that implement the systems and methods of the present invention. However, describing the invention with drawings should not be construed as imposing, on the invention, any limitations that may be present in the drawings. The present invention relates to both methods and systems for electronically tracking pressurization data. As used in this application, "pressurization data" is a broad term intended to encompass virtually any data that may be relevant in pressure related display, control, setup, or monitoring. In contrast, the term pressurization value generally indicates a measured quantity of pressure.

The terms "pressurization state" and "pressurization cycle," as used in this application, are also broad terms. Pressurization state refers to a category of pressurization data that may be of interest. In a preferred embodiment that is described below, there are two possible pressurization states, depressurization and pressurization. However, nothing in this application should be construed as limiting the present invention to distinguishing between only two pressurization states. For example, practicing the present invention may entail distinguishing between high, medium, and low states of pressurization values. Alternatively, pressurization states could be defined in terms of time intervals. Pressurization states generally are defined in terms of the conditions that are necessary for moving from one state to another, such as reaching a threshold or boundary pressurization value.

Pressurization cycle refers to moving between an arbitrary sequence of pressurization states. A preferred embodiment, described in more detail below, defines a pressurization cycle as a state of depressurization, followed by a state of pressurization, followed by returning to a state of depressurization. However, nothing in this application should be construed as limiting the present invention to any particular sequence of pressurization states.

A preferred embodiment of the present invention is useful for receiving, displaying, monitoring, and storing pressurization data during balloon coronary angioplasty, more technically known as PTCA. PTCA is a surgical procedure used in treating the narrowing of arteries that occurs in coronary artery disease. During the procedure, a balloon catheter is inserted into an artery of the groin or arm and then advanced through the artery using a guide catheter. An x-ray sensitive dye in the artery and catheters, used in conjunction with real-time x-ray techniques, aids in navigating the catheters through the body's arteries.

The balloon catheter is advanced to the site of narrowing or blockage. Once the site is reached, the balloon catheter is inflated to a pressure of approximately 7 to 10 atmospheres for a duration of about 20 to 60 seconds and then deflated. The inflation/deflation cycle is repeated several times, with pressure increasing slightly each inflation, to compress the buildup of plaque along the artery wall and thereby increase the amount of blood flow to the heart muscle. After the artery is cleared, the balloon catheter may be removed or directed to another site of narrowing or blockage.

Although the present invention is described in terms of a preferred embodiment for use in PTCA procedures as a treatment for coronary artery disease, the systems and methods of the invention are not limited to use in PTCA. It is anticipated that the present invention will be useful in a wide variety of applications where tracking pressurization data is of value. Some of these applications may include other medical uses whereas others may involve completely unrelated fields.

Figure 1B:
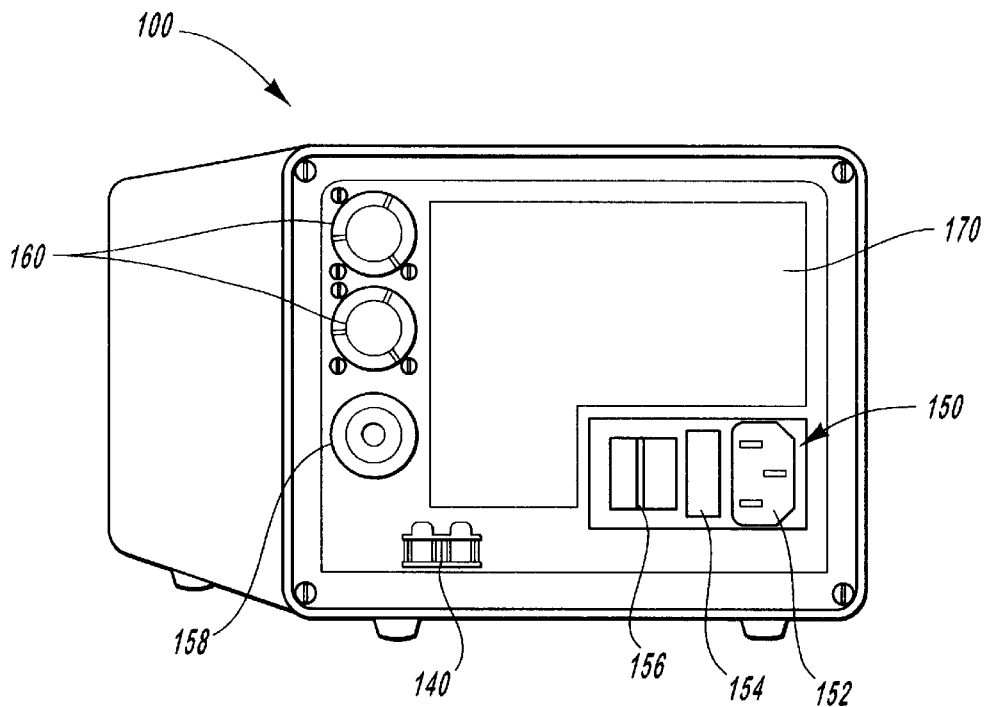

The present invention integrates various display cues, setup parameters, and control features to provide novel methods and systems for tracking pressurization data. FIGS. 1A and 1B show a preferred embodiment of an electronic controller for use in PTCA procedures, designated generally as 100. FIGS. 1A and 1B show the front and back of the controller, respectively. As shown in FIG. 1A, the controller includes Display 200, Outer Case 110, and Syringe Input Connector 130. Display 200 is a color LCD graphics display with a touch screen interface. The operational details of Display 200 are described with reference to FIGS. 2A–2D. Further information about Syringe Input Connector 130 is provided with reference to FIGS. 4 and 5. FIG. 1B shows Power Area 150 (with Power Connector 152, Fuse Holder 154, and Power Switch 156), Grounding Lug 158, Cooling Fans 160, Decal Area 170 (for serial and model numbers, manufacturer information, instructions, etc.), and Fiber Optic Connector 140. Fiber Optic Connector 140 is described in more detail with reference to FIG. 4.

Figure 2A:
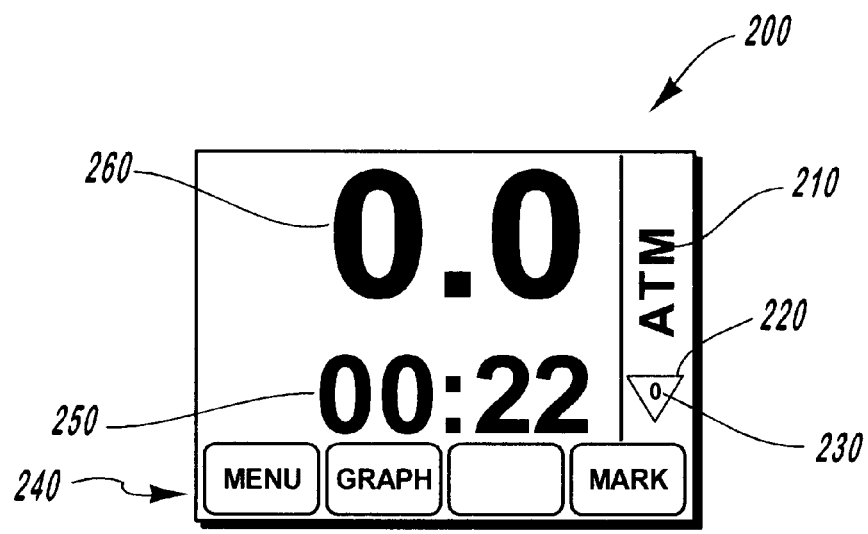
FIGS. 2A, 2B, 2C, and 2D depict various display options for pressurization data and software menu keys.

Turning now to FIGS. 2A, 2B, 2C, and 2D, the various display options for pressurization data and software menu keys ("soft keys") are shown. FIG. 2A shows Display 200 after a control syringe is connected to the electronic controller through Syringe Input Connector 130 (FIG. 1A). Pressure Unit Label 210 shows the units of measure as atmospheres, abbreviated "ATM." Pressure Reading 260 displays the pressurization value received from the control syringe. It is worth noting that although Pressure Reading 260 may be negative, zero, or positive, all pressurization values fall within two pressurization states, either depressurization or pressurization. (The details of how these two pressurization states are defined is presented below while describing Low Trigger 355 in connection with FIG. 3A.) To account for variations in pressurization values that are of minor clinical significance, Pressure Reading 260 displays zero for a range or band of pressurization values around zero. For example, in the embodiment currently being described, the band or range of values is zero ±2 psi. The present invention does not impose any particular limit on the size of the zero band. Some uses of the present invention may require a relatively narrow zero band while others may benefit from a relatively large zero band.

By pointing down, Pressurization Arrow 220 indicates depressurization as the current pressurization state. The Pressurization Number 230 within Pressurization Arrow 220 shows the number of pressurization cycles that have occurred. (For the embodiment currently being described, a pressurization cycle begins with a state of depressurization, followed by a state of pressurization, and ends with another state of depressurization. As previously indicated, the transitions between depressurization and pressurization will be 11described below along with Low Trigger 355 of FIG. 3A.)

Duration 250 displays the elapsed time for the current state of depressurization, 22 seconds. Soft Keys 240 appear along the bottom of Display 200.

Figure 2B:
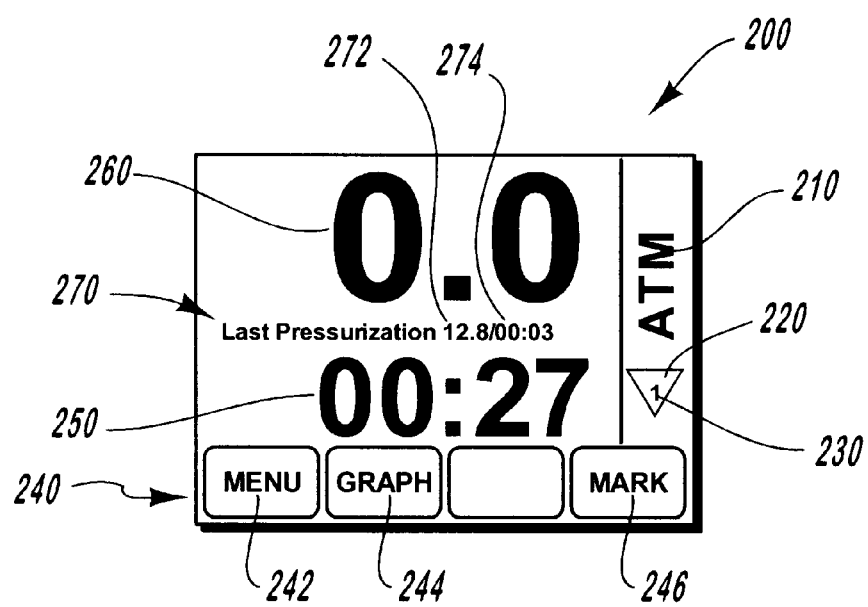

FIG. 2B also shows Soft Keys 240, including Menu Key 242, Graph Key 244, and Mark Key 246. Menu Key 242 is available under two circumstances. First, as shown in FIGS. 2A and 2B, Menu Key 242 may be selected when a control syringe is connected, but pressurization data indicates a state of no pressurization. Menu Key 242 is also displayed when no syringe is connected to Electronic Controller 100. However, as shown in FIG. 3A, Menu Key 242 provides different options based on whether or not a control syringe has been connected.

Turning briefly then to FIG. 3A, the options of Main Menu 300 are shown. If a control syringe is connected, but is not pressurized (304), History 310 and Set Units 320 are the only selections that are displayed. These selections also are available when no syringe is connected (302). History 310 is a record of pressurization data that has been stored for a particular syringe connection. The historical pressurization data does not include all pressurization data received by Electronic Controller 100. Rather, discrete events such as the peak pressure, starting time, and duration of an inflation are stored. By dividing pressurization data into discrete events, the stored information provides clinically significant data, with minimal redundancy (e.g., storing one entry describing a 30 second pressurization rather than 30 entries storing the pressurization value each second of the pressurization). Mark Key 246 (FIGS. 2B, 2C, and 2D) allows the user to identify the current readings as an event to be stored. By selecting History 310, the user may scroll through a list of the syringe histories that are stored. Once identified, the syringe history of interest may be selected in order to review the stored pressurization data for the desired syringe history.

Set Units 320 sets the default units of measure for pressurization values. Choices include atmospheres, bars, psi, mmHg, and kPa. As will be described later, a user may change the displayed units of measure, at any time. The default simply determines what units will be used in the absence of an alternate user selection.

If no syringe is connected (302), the Main Menu 300 includes two additional options, Clear 330 and Setup 350. Clear 330 erases the historical pressurization data stored in Electronic Controller 100. To avoid accidental clearings, the controller requires confirmation that all historical data should be deleted from memory when Clear 330 is selected. Setup 350 leads to a submenu of options that includes, Language 351, Time 352, Date 353, High Trigger 354, Low Trigger 355, Printer 356, and Remote 357.

FIG. 3B shows the submenu displayed when Setup 350 is selected. A column of Entry Soft Keys 360 displays along the right side of the display. Depending on the type of setup information being entered, different Entry Soft Keys 360 may be displayed. The Entry Soft Keys 360 for the Setup 350 menu include Up Arrow 362, OK 364, and Down Arrow 366. At the Setup 350 menu, it is only necessary to indicate which of the setup parameters is being changed. Language 351 is highlighted. As the screen text indicates, pressing OK 364 will lead to the language selection menu. Pressing Up Arrow 362 or Down Arrow 366 navigates the highlighting to other setup parameters. When the desired setup parameter is highlighted, selecting OK 364 allows the highlighted setup parameter to be modified. For example, Language 351 offers English, German (Deutsch), French (Francais), and Spanish (Español) as options. Once a particular language is selected, all text (prompts, menus, date formats, etc.) is displayed in the newly chosen language.

Time 352 and Date 353 set the current system date and time for Electronic Controller 100. Although not shown, Time 352 and Date 353 provide examples of Entry Soft Keys 360 that are specific to the type of setup information being entered. Both Time 352 and Date 353 include up and down arrows for altering a numerical representation of the date or time, right and left arrows for moving between digits, and an OK key for saving the changes. A flashing numeral indicates the current digit being modified. Generally, all numerical setup data is modified in this manner. Soft Keys 340 of the date/time entry include Exit 348 (similar to the Exit 348 as is shown on the Setup 350 submenu display) for canceling any changes made to the system date or time.

High Trigger 354 allows for setting a maximum pressurization value that should be received from the control syringe. When the pressurization value received from the control syringe meets or exceeds High Trigger 354 the display provides a visual alert. The present invention does not limit the visual alert to any particular form, but in Electronic Controller 100 the visual alert includes flashing the display of Pressure Reading 260 (FIGS. 2A–2D). Once pressurization values drop below High Trigger 354, the controller returns to normal continuous display.

Before describing Low Trigger 355, it may be helpful to explain the boundaries or transitions that divide a state of depressurization from a state of pressurization in the embodiment currently being described. Two threshold pressurization values are used in defining the transition between pressurization states. One value, Low Trigger 355, specifies the threshold pressurization value that divides depressurization from pressurization, starting from a current pressurization state of depressurization. In other words, if the current pressurization state is depressurization, pressurization values must reach Low Trigger 355 before the pressurization state will transition to a state of pressurization. The second value specifies the threshold pressurization value that divides pressurization from depressurization, starting from a current pressurization state of pressurization. Analogous to Low Trigger 355, this second threshold value must be crossed before the pressurization state will transition to a state of depressurization. The second threshold value is set to zero and may not be configured in this embodiment. However, nothing in this description should be interpreted to preclude the second threshold value from also being configurable or from adding additional threshold values.

Note also that the transition from depressurization to pressurization occurs when Low Trigger 355 is reached, whereas the transition from pressurization to depressurization occurs when the second threshold value is crossed (i.e., pressurization values are negative). Remember, however, that the zero band may result in a negative pressure being displayed as zero. Therefore, to a user it may appear that the transition from pressurization to depressurization occurred at zero pressure.

Selecting Printer 356 leads to the printer setup screen. Assuming a printer is attached to the controller, printer setup allows for selection between three printout modes (graph, text, and none) and a test option. "Graph mode" provides a detailed graphics printout, "text mode" produces a summarized tabular printout, and "none" disables printing. Selecting "test" sends a diagnostic printout to the printer and then returns to the printout mode that was previously selected (i.e., graph, text or none). Electronic Controller 100 also displays printer status messages such as "Printing," "Paper Out," "Busy," "Unavailable," or "Ready" to aid in troubleshooting printer operation.

Remote 357 allows for enabling or disabling remote operation of a controller. The operation of a remote electronic controller will be described in conjunction with FIGS. 4 and 5. At this time, it is sufficient to recognize that a controller may operate in either host or remote mode and that Remote 357 enables or disables this feature.

Returning again to FIG. 2B, the operation of Display 200 will be described in more detail. As indicated above, Display 200 includes a touch interface. One of the touch entries supported is the ability to change the units of measure for Pressure Reading 260. Electronic Controller 100 is capable of displaying Pressure Reading 260 in atmospheres, bars, psi, mmHg, and kPa. With each touch of Pressure Unit Label 210, the controller cycles through the units of measure options one at a time. A change to Pressure Unit Label 210 includes converting the value displayed by Pressure Reading 260 to the newly selected units of measure.

In FIG. 2B, Pressurization Number 230 has been increased to a value of "1." This means that the first pressurization cycle is in process. Prior Pressurization 270 shows the Prior Peak Pressure 272 and Prior Duration 274. The maximum pressure reached during the prior pressurization cycle of 3 seconds was 12.8 atmospheres. When Prior Pressurization 270 is displayed, changing Pressure Unit Label 210 converts both the value displayed by Pressure Reading 260 and the value displayed by Prior Peak Pressure 272 to the newly selected units of measure. Note that Pressure Reading 260 and Pressurization Arrow 220 indicates that Electronic Controller 100 is receiving pressurization data indicating a state of depressurization. According to Duration 250, the current state of depressurization has a total elapsed time of 27 seconds.

Duration 250 is limited to 99 minutes and 59 seconds for display purposes. After that limit is exceeded, Display 200 will provide a visual alert to indicate that the elapsed time is no longer accurate. The present invention does not necessary impose any particular limit on Duration 250 or on the type of visual alert provided if an established time limit is exceeded. Nevertheless, in the PTCA embodiment of Electronic Controller 100, Duration 250 is limited to 99 minutes and 59 seconds and Duration 250 will flash when that limit is exceeded.

Figure 2C:
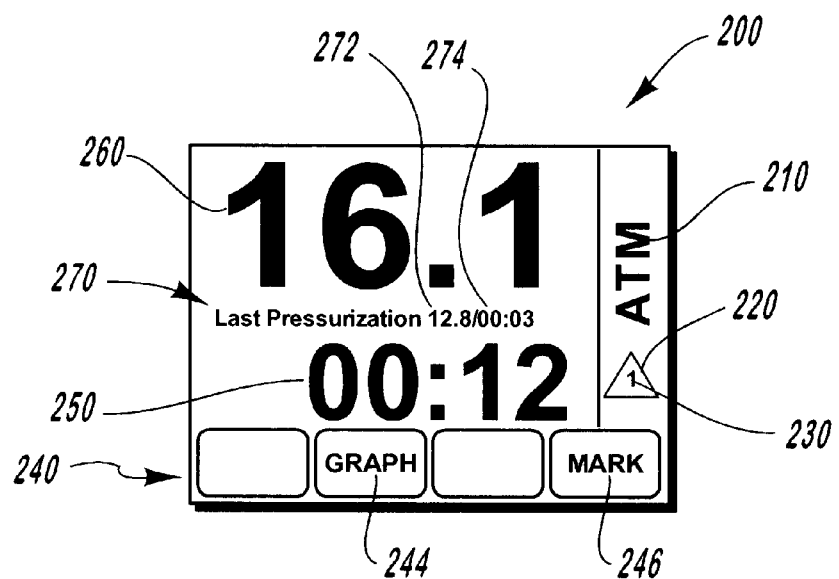

Moving next to FIG. 2C, as Electronic Controller 100 receives pressurization data indicating a state of pressurization, the background color of Display 200 changes from a bluish-red to green. The bluish-red color indicates a state of depressurization and green indicates a state of pressurization. In FIG. 2C, Pressure Reading 260 indicates a pressurization value of 16.1 atmospheres. Because the received pressurization data indicates a state of pressurization, Pressurization Arrow 220 points up. As indicated by Pressurization Number 230, pressurization values have exceeded Low Trigger 355 on two occasions, once during Prior Pressurization 270 and once for the current Pressure Reading 260 of 16.1 atmospheres.

Figure 2D:
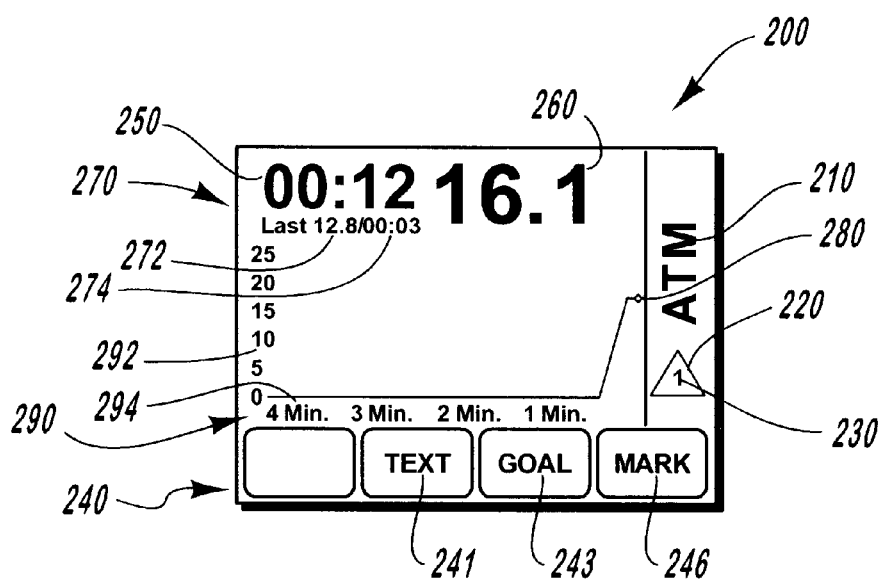

Making the transition between a state of depressurization, as shown in FIGS. 2A and 2B, to a state of pressurization, as shown in FIGS. 2C and 2D, also restarts the elapsed time display. Duration 250 indicates that Electronic Controller 100 has been receiving pressurization values in excess of the Low Trigger 355 (FIGS. 3A and 3B) for 12 seconds. In PTCA procedures, this means that a control syringe has been applying pressure to a balloon catheter for that elapsed time.

Selecting Graph 244 from Soft Keys 240 changes the display of Electronic Controller 100 to the graph mode illustrated in FIG. 2D. Essentially the same information is presented in graph mode as in text mode. Display 200 shows a current Pressurization Reading 260 of 16.1 atmospheres during the current state of pressurization's elapsed time of 12 seconds (Duration 250). Pressurization Arrow 220 is pointing up due to the pressurization indicated by Pressure Reading 260. Prior Pressurization 270 shows a Prior Peak Pressure 272 of 12.8 atmospheres and a Prior Duration 274 of 3 seconds. Pressurization Number 230 remains unchanged from FIG. 2C.

The primary difference between FIGS. 2C and 2D is the presence of Pen 280 and Scales 290, including Pressure Scale 292 and Time Scale 294. Pressure Scale 292 and Time Scale 294 form a grid for graphing pressurization data. Initially, Pressure Scale 292 shows the full range of possible pressurization values. (When Pressure Unit Label 210 indicates mmHg as the units of measure, Electronic Controller 100 limits pressurization values to 9999 mmHg for display purposes. Electronic Controller 100 is capable of operating with pressurization values up to approximately 25 atmospheres. However, the present invention does not necessarily impose any requirement for establishing a maximum pressurization value, for display purposes or otherwise.) Pen 280 draws the current pressurization value at the right side of the display in a continuous manner. Placing the current pressurization at the right, with prior pressurization values moving to the left, mimics the operation of most medical instrumentation, making Electronic Controller 100 more intuitive to use.

Just as described with reference to FIGS. 2B and 2C, Display 200 includes a touch interface. However, several differences between text mode and graph mode operation will become readily apparent. First, changes to the units of measure will require adjusting Pressure Scale 292 in addition to converting Pressure Reading 260 and Prior Peak Pressure 272. Furthermore, an additional feature available in graph mode is the ability to zoom. Zooming reduces the size of Pressure Scale 292 to show finer detail in pressurization value changes. The zoom function is activated and deactivated by touching Pressurization Arrow 220.

In zoom mode, Pressure Scale 292 is divided by four divisions. The size of the divisions depends on the units of measure indicated by Pressure Unit Label 210. When Pressure Unit Label 210 is atmospheres or bars, the divisions are 1 unit apart; for psi and kPa, the divisions are 10 units apart; and, the divisions are 100 units apart for mmHg. Depending on the units of measure, Pressure Scale 292 uses integer values (atm, bar), integer values divisible by 10 (psi, kPa) or integer values division by 100 (mmHg). These four divisions produce three regions of pressurization values. For example, if Pressure Scale 292 ranges from 3–6 atmospheres (with divisions at 3, 4, 5, and 6 atmospheres), the corresponding three ranges would include 3–4 atmospheres, 4–5 atmospheres, and 5–6 atmospheres.

The initial range of Pressure Scale 292 is calculated to show the current pressurization value in roughly the middle of the scale. With the three-region arrangement described above, the approach for roughly centering the current pressurization value is relatively straightforward. The process simply entails providing one full region below and one full region above the current pressurization value. For example, the three regions described above would result from a current pressurization value of 4.3 atmospheres. Division sizes of 10 or 100 are processed in an analogous manner. In other words, Pressure Scale 292 would range from 30–60 psi or 300–600 mmHg for current pressurization values of 43 psi or 430 mmHg, respectively.

Once activated, the zoom feature uses auto-ranging to update Pressure Scale 292. Auto-ranging is a feature that dynamically adjusts the pressurization values included within Pressure Scale 292. To keep the currently displayed pressurization value roughly in the middle of Pressure Scale 292, auto-ranging recalculates Pressure Scale 292 when pressurization values near the scale's endpoints. Auto-ranging defines borders at the edges of Pressure Scale 292 that are 60% of a division wide. Whenever pressurization values fall within the 60% border, auto-ranging recalculates Pressure Scale 292. For example, if Pressure Scale 292 included pressurization values from 3 to 6 atmospheres with divisions every 1 atmosphere, auto-ranging would recalculate Pressure Scale 292 when pressurization values reach either 3.6 atmospheres or 5.4 atmospheres. Auto-ranging adjusts Pressure Scale 292 by 1 division. Thus, in the example provided above, if pressurization values reached 3.6 atmospheres, Pressure Scale 292 would be adjusted to range from 2 to 5 atmospheres. Naturally, the range of pressurization values covered by Pressure Scale 292 is also recalculated when the units of measure are changed.

The foregoing description of zoom mode and auto-ranging is intended as exemplary only and not as necessarily imposing any particular limitation on the scope of the present invention. A wide variety of similar criteria could be used to produce equivalent results. For example, the size of the divisions may be dynamically calculated based on how quickly pressurization values are changing, the current pressurization value could be placed exactly in the center of Pressure Scale 292, Pressure Scale 292 could range from any arbitrary pressurization value to another, or the size of the borders used in auto-ranging could be adjusted. Alternatively, zoom mode could be implemented as showing any one of several predefined regions of pressurization values.

Graph mode also includes the ability to set a target or goal pressurization value. Selecting Goal Key 243 places a reference pressurization goal line across Display 200. Touch selectable up and down arrows along the right side (like Entry Soft Keys 360 of FIG. 3B) allow the goal line to be moved to a desired pressurization value. Once in place, selecting an OK key places the pressurization goal line on the display. (In FIG. 2D, the pressurization goal line would appear as a horizontal blue line at the chosen pressurization value.) Pressing Goal Key 243 twice removes (disables) the pressurization goal line.

Another feature of graph mode is a visual indication for marked events. When Mark Key 246 is selected in graph mode, a yellow dashed vertical line is displayed to indicate the pressurization data at that time has been marked as an event. As described above, marked events are noted in the syringe history for later review. Pressing Text Key 241 returns Display 200 to text mode.

Figure 4:
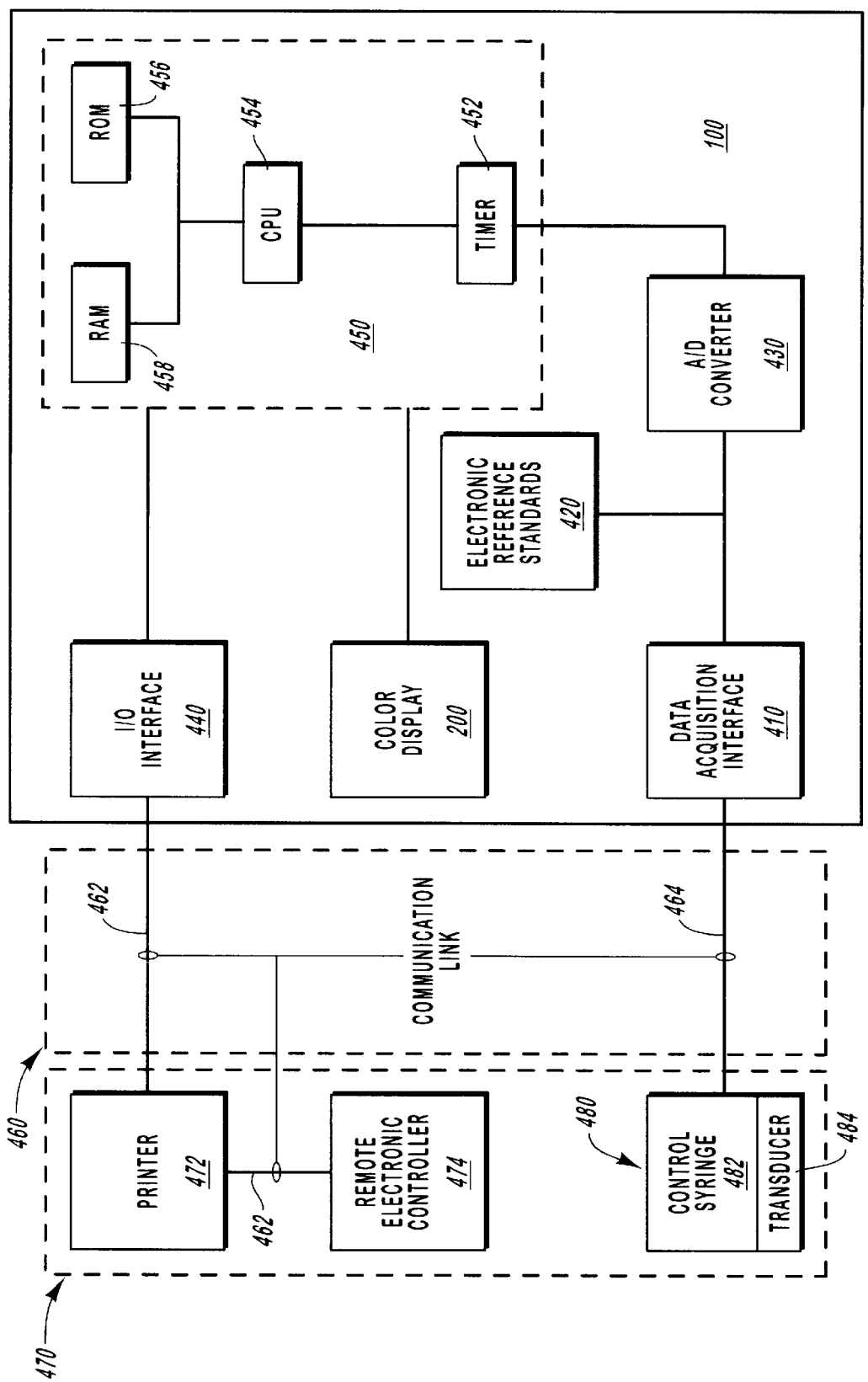
FIG. 4 depicts a block diagram of a system for acquiring, displaying, storing, and monitoring pressurization data according to the present invention.

FIG. 4 presents a block diagram of a system for acquiring, displaying, storing, and monitoring pressurization data according to the present invention. Included within the system are Electronic Controller 100, Peripheral Devices 470, and Communication Links 460. Peripheral Devices 470 include Control Syringe 480. Control Syringe 480 has two basic components, Syringe 482 and Transducer 484.

One example of Syringe 482 and Transducer 484 is described in U.S. Pat. No. 5,300,027, previously incorporated herein by reference. Syringe 482 is capable of generating either a positive or negative pressure. During PTCA procedures, the generated pressure is used to inflate and deflate a balloon catheter. Transducer 484 converts the generated pressure into electrical signals for processing. The electrical signals produced by Transducer 484 are transferred to Electronic Controller 100 through Communication Link 464 and Data Acquisition Interface 410. (Data Acquisition Interface 410 includes Syringe Input Connector 130 as shown in FIG. 1A.)

The present invention does not impose any particular limitations on Communication Link 464 and Data Acquisition Interface 410. In the PTCA embodiment described herein, Communication Link 464 is a cable that carries electrical signals and Data Acquisition Interface 410 is a keyed electrical connection with some filtering hardware to condition the received signal. Alternative implementations may include a wireless, optical, sonic, or some other link capable of transferring pressurization data from Syringe 482 to Electronic Controller 100.

After the pressurization data is received through Data Acquisition Interface 410, A/D Converter 430 converts the analog signals generated by Transducer 484 to digital quantities suitable for processing by Processing Hardware 450. Processing Hardware 450 includes CPU 454, Timer 452, ROM 456, and RAM 458. Here again, the present invention does not impose any particular requirements on Processing Hardware 450 other than those described in the appended claims. Processing Hardware 450 (executing relevant program code instructions) is one example of a processor means for performing the various steps required by the present invention. A processor means as used in the present invention may include generic digital processors as well as specialized signal and/or display processors. In a preferred embodiment, CPU 454 is a generic digital processing unit.

Processing Hardware 450 integrates Timer 452 to facilitate the various time measurements that occur in practicing the present invention, such as tracking the elapsed time of pressurization/depressurization and other internal events that are regularly monitored. ROM 456 is primarily used to store program instructions that govern the operation of Electronic Controller 100. (The operation of Electronic Controller 100 is described in more detail below, with respect to FIG. 5.) RAM 458 includes volatile and non-volatile portions. The volatile portion of RAM 458 is used as a memory space for CPU 454. The non-volatile portion of RAM 458 stores the syringe histories described in conjunction with FIG. 3A and setup/configuration settings, such as the default units of measure, etc. When power to Electronic Controller 100 is shut off, a backup battery retains the information stored in the non-volatile portion of RAM 458.

Electronic Controller 100 also includes Electronic Reference Standards 420. Electronic Reference Standards 420 are an electronic representation of two pressurization values, a high value and a low value. Reading the Electronic Reference Standards 420 allows Electronic Controller 100 to verify that it is operating correctly over the device's useful lifetime. The details of how Electronic Controller 100 interacts with Electronic Reference Standards 420 are described below, with reference to FIG. 5.

Display 200 of Electronic Controller 100 is a color LCD graphics display. As described above, Display 200 includes a touch interface so that interaction with Electronic Controller 100 may be accomplished without the need for an external input device, such as a mouse or a keyboard. However, the present invention does not necessarily require that input only occur through the touch interface of Display 200.

I/O Interface 440 and Communication Link 462 allow Electronic Controller 100 to communicate with Peripheral Devices 470, including Printer 472 and Remote Electronic Controller 474. Communication Link 462 and I/O Interface 440 are implemented as an optical fiber communication channel. (I/O Interface 440 includes Fiber Optic Connector 140 as shown in FIG. 1B.) However, like Communication Link 464 and Data Acquisition Interface 410, the present invention does not necessarily impose any particular limitation on the technology used to implement I/O Interface 440 and Communication Link 462. Alternative implementations may include a wireless, electrical, sonic, or some other link capable of transferring data from Electronic Controller 100 to Peripheral Devices 470.

As described above with reference to the Printer 356 setup option of Main Menu 300 (FIG. 3A), Printer 472 may operate in several modes. Graph mode provides a detailed graphics printout and text mode produces a summarized tabular printout. Selecting test sends a diagnostic printout to Printer 472. As part of the interaction that occurs through Communication Link 462, Electronic Controller 100 displays various printer status messages, including "Printing," "Paper Out," "Busy," "Unavailable," or "Ready." As shown in FIG. 4, multiple Peripheral Devices 470 may be daisy-chained together using Communication Link 462. That is, both Printer 472 and Remote Electronic Controller 474 may be connected to Electronic Controller 100 at the same time through Communication Link 462.

Remote Electronic Controller 474 allows all of the functions of Electronic Controller 100 (termed a primary or host controller) to be controlled through a remote device. For example, the units of measure and display modes, text or graph, of both devices may be controlled through either device. While the functionality of the host, Electronic Controller 100, is duplicated at Remote Electronic Controller 474, historical data is stored only at the host device. Furthermore, Remote Electronic Controller 474 ignores any control syringe that is connected while operating as a remote device. The Remote Electronic Controller 474 is substantially identical to Electronic Controller 100. To be considered substantially identical, Remote Electronic Controller 474 and Electronic Controller 100 must share a compatible I/0 Interface 440 so that the devices may communicate with each other and support similar or complementary display and/or control features. Although a preferred embodiment for use in PTCA procedures includes a Remote Electronic Controller 474 and "host" Electronic Controller 100 that support identical display and control features, the present invention does not require the devices to be identical in that way.

Figure 5:
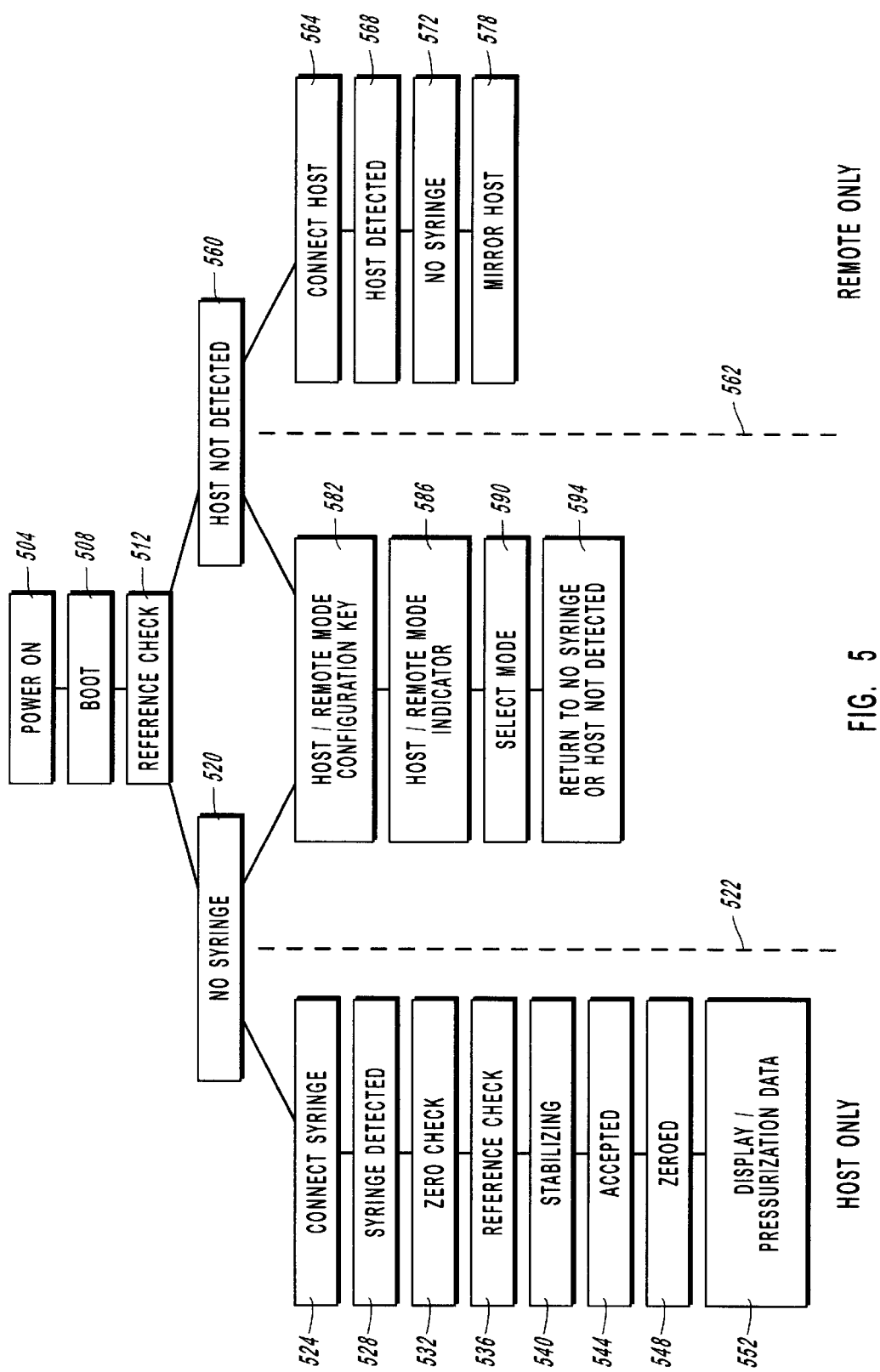
FIG. 5 shows a flow chart of the electronic controller's operating states.

FIG. 5 shows a flow chart for use in describing the operation of Electronic Controller 100. Electronic Controller 100 is capable of functioning in either remote or host mode. Features on the "Host Only" side of Dashed Line 522 relate to Electronic Controller 100 operating in host or primary mode, features on the "Remote Only" side of Dashed Line 562 relate to Electronic Controller 100 operating in remote mode, and features between Dashed Lines 522 and 562 are for changing the configuration of Electronic Controller 100 between remote and host modes.

When Electronic Controller 100 is Powered On 504, the device initializes itself by performing a Boot Operation 508. Following the Boot Operation 508, Electronic Controller makes a Reference Check 512 of Electronic Reference Standards 420 (FIG. 4). The first time Electronic Controller 100 is Powered On 504, the values represented by Electronic Reference Standards 420 are stored in a non-volatile area of RAM 458 (FIG. 4). When Electronic Controller 100 is Powered On 504 subsequent to the first time, the Reference Check 512 compares the previously stored values of Electronic Reference Standards 420 with newly read values of Electronic Reference Standards 420. If the stored values and newly read values vary by more than an allowable tolerance, Electronic Controller 100 displays an error message and will not operate.

Reference Check 512 has two components, reading the high pressure reference and the low pressure reference of Electronic Reference Standards 420. The tolerance for these readings is defined by establishing a range or window of values that are acceptable for each reference standard. For example, the high pressure reference standard has a maximum acceptable high value and a minimum acceptable high value. Any reading of the high pressure reference standard must fall within the high window to pass the tolerance requirement. Likewise, the low pressure reference standard has a minimum acceptable low value and a maximum acceptable low value. Any reading of the low pressure reference standard must fall within the low window to pass the tolerance requirement.

If operating in host mode, Electronic Controller 100 then displays a message indicating that no syringe has been connected (520). Once a syringe is connected (524), Electronic Controller 100 acknowledges that a syringe has been detected (528). Electronic Controller 100 then performs several checks to insure that both Control Syringe 480 (FIG. 4) and Electronic Controller 100 are operating correctly. A Zero Check 532 of Control Syringe 480 is performed to insure that the control syringe is not pressurized when connected. The zero check allows for minor variations, but requires essentially no pressurization (i.e., pressurization values equivalent to ambient air pressure) of the control syringe when the control syringe is connected. After the Zero Check 532, a Reference Check 536, like Reference Check 512, is performed. Stabilizing 540 requires that the pressurization data received from the control syringe remain essentially constant during the stabilization period. If any of the checks fail, Electronic Controller 100 displays an appropriate error message.

The checks require only a few seconds to complete. When the checks succeed, Electronic Controller 100 displays a message indicating that the control syringe has been accepted (544). Once accepted, Electronic Controller 100 zeros the control syringe (548). In other words, Electronic Controller 100 interprets the pressurization data it receives from the control syringe as indicating zero or no pressurization. After zeroing, Electronic Controller 100 is ready to Display Pressurization Data 552.

When operating in remote mode, Electronic Controller 100 displays a message indicating that no host is detected (560) after performing Reference Check 512. Once a host connection (564) is made, Electronic Controller 100 acknowledges detecting the host (568). After detecting a host, Electronic Controller 100 displays that no syringe is connected (572), indicating that the host (not the remote) does not have a control syringe connected. From this point on, the Electronic Controller 100 operating as a remote device mirrors the display of the host device (578).

Regardless of operating mode, Electronic Controller 100 may be configured to operate in host mode or remote mode prior to the connection of a control syringe or the connection of a host. At the no syringe message (520) or host not detected message (560), a host/remote mode configuration key may be selected (582). In a preferred embodiment for performing PTCA procedures, the host/remote mode configuration key is a question mark displayed on Display 200. Once the host/remote mode configuration key is selected (582), Electronic Controller 100 displays a host/remote mode indicator (586). Again, in a preferred embodiment for performing PTCA procedures, the host mode indicator is an "H" and the remote mode indicator is an "R," each displayed in the upper right-hand corner of Display 200. The touch screen interface allows for pressing either the "H" or "R" to select the operating mode (590). By pressing the "H" or "R," Electronic Controller 100 toggles operation from host to remote (pressing "H") or from remote to host (pressing "R"), based on the mode of operation at the time either "H" or "R" is pressed. If remote mode is selected, Electronic Controller 100 returns (594) to the host not detected message (560). If host mode is selected, Electronic Controller 100 returns (594) to the no syringe message (520).

The present invention may be embodied in other forms without departing from its spirit or essential characteristics. As properly understood, the preceding description of specific embodiments is illustrative only and in no way restrictive. The scope of the invention is, therefore, indicated solely by the appended claims as follows.

What is claimed and desired to be secured by U.S. letters patent is:

1. In a real-time primary device including a display that displays received pressurization data, a method of electronically tracking the received pressurization data, the method comprising the acts of:

establishing a plurality of pressurization states;

receiving pressurization data that includes pressurization values corresponding to more than one of the plurality of pressurization states; and changing the background color of the display as the pressurization values transition between any of the plurality of pressurization states.

2. A method as recited in claim 1 wherein the plurality of pressurization states include a state of pressurization and a state of depressurization, the method further comprising the act of displaying a pressurization arrow indicating whether a most recent pressurization value represents a state of pressurization or a state of depressurization.

3. A method as recited in claim 2 further comprising the acts of:

defining a pressurization cycle in terms of the plurality of pressurization states; and displaying within the pressurization arrow, a count corresponding to a current pressurization cycle.

4. A method as recited in claim 1 further comprising the acts of:

defining a zero band of pressurization values;

displaying a current pressurization value as zero when it falls within the zero band of pressurization values;

displaying a unit of measure corresponding to the current pressurization value; and displaying an elapsed time since a last transition between any of the plurality of pressurization states.

5. A method as recited in claim 4 further comprising the acts of:

defining a pressurization cycle in terms of the plurality of pressurization states;

receiving pressurization data that corresponds to a complete pressurization cycle;

displaying a pressurization value corresponding to a maximum pressurization value reached during the complete pressurization cycle; and displaying an elapsed time of at least one pressurization state that occurred during the complete pressurization cycle.

6. A method as recited in claim 5 wherein the primary device is capable of tracking pressurization values in at least two units of measure, the units of measure arranged in a circular sequence, and wherein the display is a graphical display that includes a touch interface, the method further comprising the acts of:

receiving a touch input corresponding to the display of a unit of measure;

displaying the unit of measure that is next in the circular sequence; and updating the display of pressurization values to reflect the displayed unit of measure.

7. A method as recited in claim 6 further comprising the acts of:

displaying one or more soft keys on the graphical display, one of the soft keys providing the capability of marking current pressurization data to define an event;

receiving a touch input corresponding to the soft key for marking events; and marking the pressurization data as an event.

8. A method as recited in claim 1 wherein the primary device includes memory, the method further comprising the acts of:

dividing pressurization data into one or more discrete events; and storing the one or more discrete events in the memory.

9. A method as recited in claim 1 wherein the primary device includes an external interface that provides pressurization data to one or more external components, the method further comprising the act of downloading pressurization data through the external interface.

10. A method as recited in claim 1 further comprising the acts of:

setting a maximum pressurization value;

setting a maximum elapsed time for any of the plurality of pressurization states;

using the display to signal if the maximum pressurization value is exceeded; and using the display to signal if the maximum elapsed time is exceeded.

11. A method as recited in claim 1 wherein the primary device includes one or more pressure reference standards, the method further comprising the acts of:

measuring the one or more pressure reference standards for a first time to produce a first pressure value for each standard; and storing the first pressure value for each standard.

12. A method as recited in claim 11 wherein the primary device includes a low pressure reference standard and a high pressure reference standard, the method further comprising the acts of:

initializing the primary device by performing the acts of:
        establishing a tolerance value indicating the allowable variation between measurements of the pressure reference standards;
        measuring the low pressure reference standard subsequent to the first time of measuring the low pressure reference standard;
        comparing the subsequent measurement of the low pressure reference standard to the first, stored, measurement of the low pressure reference standard;
        measuring the high pressure reference standard subsequent to the first time of measuring the high pressure reference standard;

comparing the subsequent measurement of the high pressure reference standard to the first, stored, measurement of the high pressure reference standard; and reporting any variation between first and subsequent measurements of the pressure reference standards, if the variation exceeds the tolerance value;

stabilizing the primary device by requiring received pressurization data to include pressurization values that remain constant during a stabilization period; and calibrating the primary device by requiring received pressurization data to include pressurization values, remaining constant during a calibration period, that essentially represent ambient air pressure.

13. A method as recited in claim 1 further comprising the act of linking a remote device to the primary device, wherein the remote device is substantially identical to the primary device.

14. A method as recited in claim 13 further comprising the acts of:

transmitting received pressurization data from the primary device to the remote device;

synchronizing the displays of the primary and remote devices;

allowing either device to receive input for controlling how the primary and remote devices operate;

transmitting any input received at the primary device to the remote device and any input received at the remote device to the primary device; and synchronizing the operation of remote and primary devices when any input is transmitted between the remote and primary devices.

15. In a real-time primary device including a graphical display that displays received pressurization data, a method of electronically tracking the received pressurization data, the method comprising the acts of:

displaying a two-dimensional grid with a first axis corresponding to time and a second axis corresponding to magnitude, the grid including divisions and a scale for indicating the values that may be represented on the grid;

displaying a magnitude indicator on the magnitude axis of the grid;

receiving pressurization data including pressurization values;

moving the magnitude indicator to a point on the magnitude axis that corresponds to the pressurization values as they are received;

drawing a point on the grid at the magnitude indicator;

scrolling the grid away from the magnitude axis to indicate the passage of time; and auto-ranging the display of the grid.

16. A method as recited in claim 15 further comprising the acts of:

setting a goal corresponding to a desired pressurization value; and drawing a line across the grid at the magnitude that corresponds to the goal.

17. A method as recited in claim 15 wherein the graphical display includes a touch interface, further comprising the act of receiving a touch input.

18. A method as recited in claim 17 wherein the touch input corresponds to a command for magnifying display of the grid, the method further comprising the act of magnifying display of the grid in a region that is roughly centered about a current pressurization value.

19. A method as recited in claim 17 further comprising the acts of:

displaying one or more soft keys on the graphical display, one of the soft keys providing the capability of marking current pressurization data to define an event, wherein the received touch input corresponds to the soft key for marking events; and marking the current pressurization data as an event.

20. A method as recited in claim 15, further comprising the acts of:

dividing the grid into regions; and auto-ranging by keeping at least one region above and one region below the position of the magnitude indicator.

21. A method as recited in claim 15 further comprising the acts of:

establishing a plurality of pressurization states;

receiving pressurization data that includes pressurization values corresponding to more than one of the plurality of pressurization states; and changing the background color of the display as the pressurization values transition between any of the plurality of pressurization states.

22. A method as recited in claim 21, wherein the pressurization states include a state of pressurization and a state of depressurization, the method further comprising the acts of:

defining a zero band of pressurization values;

displaying a current pressurization value as zero when it falls within the zero band of pressurization values;

displaying an elapsed time since a last transition between any of the plurality of pressurization states;

defining a pressurization cycle in terms of the plurality of pressurization states;

receiving pressurization data that corresponds to a complete pressurization cycle;

displaying an elapsed time of at least one pressurization state that occurred during the complete pressurization cycle;

displaying a pressurization value corresponding to a maximum pressurization value reached during the complete pressurization cycle;

displaying a unit of measure corresponding to displayed pressurization values;

displaying a pressurization arrow indicating whether a most recent pressurization value represents a state of pressurization or a state of depressurization; and displaying within the pressurization arrow, a count corresponding to a current pressurization cycle.

23. A method as recited in claim 15 wherein the primary device includes memory, the method further comprising the acts of:

dividing pressurization data into one or more discrete events; and storing the one or more discrete events in the memory.

24. A method as recited in claim 15 wherein the primary device includes an external interface that provides pressurization data to one or more external components, the method further comprising the act of downloading pressurization data through the external interface.

25. A method as recited in claim 24 wherein the act of downloading pressurization data includes downloading one of a textual representation of pressurization data and a graphical representation of pressurization data.

26. In a real-time system comprising a control syringe for generating pressure, a transducer for converting sensed pressure into electrical signals, a primary device with a graphical display that includes a touch interface, and a communication link between the transducer and primary device, a method of electronically tracking received pressurization data at the primary device, the method comprising the acts of:

establishing a plurality of pressurization states that include a state of pressurization and a state of depressurization;

receiving pressurization data that includes pressurization values corresponding to more than one of the plurality of pressurization states;

changing the background color of the display as the pressurization values transition between any of the plurality of pressurization states;

displaying a pressurization arrow indicating whether a most recent pressurization value represents a state of pressurization or a state of depressurization;

defining a pressurization cycle in terms of the plurality of pressurization states; and displaying within the pressurization arrow, a count corresponding to a current pressurization cycle.

27. A method as recited in claim 26 wherein the primary device includes memory, further comprising the acts of:

dividing pressurization data into one or more discrete events; and storing the one or more discrete events in the memory.

28. A method as recited in claim 26 further comprising the acts of:

defining a zero band of pressurization values;

displaying a current pressurization value as zero when it falls within the zero band of pressurization values;

displaying an elapsed time since a last transition between any of the plurality of pressurization states;

defining a pressurization cycle in terms of the plurality of pressurization states;

receiving pressurization data that corresponds to a complete pressurization cycle;

displaying a pressurization value corresponding to a maximum pressurization value reached during the complete pressurization cycle;

displaying a unit of measure corresponding to the displayed pressurization values; and displaying an elapsed time of at least one pressurization state that occurred during the complete pressurization cycle.

29. A method as recited in claim 28 wherein the primary device is capable of tracking pressurization values in at least two units of measure, the units of measure arranged in a circular sequence, the method further comprising the acts of:

receiving a touch input corresponding to the display of a unit of measure;

displaying the unit of measure that is next in the circular sequence; and updating the display of pressurization values to reflect the displayed unit of measure.

30. A method as recited in claim 28 further comprising the acts of:

displaying a two-dimensional grid with a horizontal axis corresponding to time and a vertical axis corresponding to magnitude, the grid including divisions and a scale for indicating the values that may be represented on the grid;

displaying a magnitude indicator at the right-hand side of the grid;

receiving pressurization data including pressurization values;

moving the magnitude indicator to a point on the vertical axis that corresponds the pressurization values as they are received;

drawing a point on the grid at the magnitude indicator;

scrolling the grid from right to left along the horizontal axis to indicate the passage of time;

setting a goal corresponding to a desired pressurization value; and drawing a line across the grid at the magnitude that corresponds to the pressurization value goal.

31. A method as recited in claim 30 wherein the primary device includes a low pressure reference standard and a high pressure reference standard, the method further comprising the acts of:

measuring the low pressure reference standard for a first time;

storing the first low pressure reference standard measurement;

measuring the high pressure reference standard for a first time;

storing the first high pressure reference standard measurement;

establishing a tolerance value indicating the allowable variation between first and subsequent measurements of the low and high pressure reference standards;

measuring the low pressure reference standard subsequent to the first time of measuring the low pressure reference standard;

comparing the subsequent measurement of the low pressure reference standard to the first, stored, measurement of the low pressure reference standard;

measuring the high pressure reference standard subsequent to the first time of measuring the high pressure reference standard;

comparing the subsequent measurement of the high pressure reference standard to the first, stored, measurement of the high pressure reference standard; and reporting any variation between first and subsequent measurements of the pressure reference standards when the variation exceeds the tolerance value.

32. A method as recited in claim 26 wherein the system includes a remote device substantially identical to and linked to the primary device, further comprising the acts of:

transmitting received pressurization data from the primary device to the remote device;

synchronizing the displays of the primary and remote devices;

allowing either device to receive input for controlling how the primary and remote devices operate;

transmitting any input received at the primary device to the remote device and any input received at the remote device to the primary device; and synchronizing the operation of remote and primary devices when any input is transmitted between the remote and primary devices.

33. A real-time primary system for electronically tracking received pressurization data, the primary system comprising:

a central processing unit;

memory coupled to the central processing unit;

a pressurization data input interface coupled to the central processing unit;

a color graphical display coupled to the central processing unit; and processor means for performing the steps of:
  establishing a plurality of pressurization states;
  receiving pressurization data that includes pressurization values corresponding to more than one of the plurality of pressurization states;
  defining a zero band of pressurization values;
  displaying a current pressurization value as zero when it falls within the zero band of pressurization values; and
  changing the background color of the display as the pressurization values transition between any of the plurality of pressurization states.

34. A system as recited in claim 33 wherein the pressurization states include a state of pressurization and a state of depressurization, the system further comprising processor means for performing the steps of:
  displaying a pressurization arrow indicating whether a current pressurization value represents a state of pressurization or a state of depressurization;
  defining a pressurization cycle in terms of the plurality of pressurization states; and
  displaying within the pressurization arrow, a count corresponding to a current pressurization cycle.

35. A system as recited in claim 34 further comprising processor means for performing the steps of:
  displaying an elapsed time since a last transition between any of the plurality of pressurization states;
  receiving pressurization data that corresponds to a complete pressurization cycle;
  displaying a pressurization value corresponding to a maximum pressurization value reached during the complete pressurization cycle;
  displaying a unit of measure corresponding to the displayed pressurization values; and
  displaying an elapsed time of at least one pressurization state that occurred during the complete pressurization cycle.

36. A system as recited in claim 35 further comprising a touch interface integral with the color graphical display.

37. A system as recited in claim 36 further comprising processor means for performing the steps of:
  displaying one or more soft keys on the graphical display, one of the soft keys providing the capability of marking current pressurization data to define an event;
  receiving a touch input corresponding to the soft key for marking events; and
  marking the current pressurization data as an event.

38. A system as recited in claim 36 wherein the primary device is capable of tracking pressurization values in at least two units of measure, the units of measure arranged in a circular sequence, further comprising processor means for performing the steps of:
  displaying a unit of measure corresponding to a current pressurization value;
  receiving a touch input corresponding to the display of the unit of measure;
  displaying the unit of measure that is next in the circular sequence; and
  updating the display of pressurization values to reflect the displayed unit of measure.

39. A system as recited in claim 33 further comprising processor means for performing the steps of:
  dividing pressurization data into one or more discrete events; and
  storing the one or more discrete events in the memory.

40. A system as recited in claim 33 further comprising:
  an external interface that provides pressurization data to one or more external components; and
  processor means for transferring data through the external interface.

41. A system as recited in claim 33 further comprising:
  one or more pressure reference standards; and
  processor means for performing the steps of:
    measuring the one or more pressure reference standards for a first time to produce a first pressure value for each standard;
    storing the first pressure value for each standard;
    measuring each standard subsequent to the first time to produce a subsequent pressure value for each standard;
    comparing the first pressure value and subsequent pressure value for each standard; and
    reporting, for each standard, any variation between the first and subsequent pressure values when the variation is greater than a tolerance value.

42. A system as recited in claim 33 further comprising:
  a remote system interface;
  a remote system that is substantially identical to the primary system; processor means for performing the steps of:
    establishing a connection between the primary system and the remote system;
    transmitting received pressurization data from the primary system to the remote system;
    synchronizing the displays of the primary and remote systems;
    receiving, from either device, input for controlling how the primary system and remote system operate;
    transmitting any input received at the primary system to the remote system and any input received at the remote system to the primary system; and
    synchronizing the operation of the remote and primary systems when any input is transmitted between the systems.

43. A system as recited in claim 33 further comprising processor means for performing the steps of:
  displaying a two-dimensional grid, the grid having a first axis corresponding to time and a second axis corresponding to magnitude;
  displaying a magnitude indicator on the magnitude axis;
  moving the magnitude indicator to a point on the magnitude axis that corresponds to pressurization values as they are received;
  drawing a point on the grid at the magnitude indicator; and
  scrolling the grid away from the magnitude indicator to indicate the passage of time.

44. A system as recited in claim 43 further comprising processor means for performing the steps of:
  setting a goal corresponding to a desired pressurization value; and
  drawing a line across the grid at the magnitude that corresponds to the pressurization value goal.

45. A system as recited in claim 44 further comprising:

a touch interface integral with the color graphical display; and processor means for performing the steps of:
- receiving a touch input that corresponds to a command for magnifying display of the grid; and
- magnifying display of the grid in a region that is roughly centered about a current pressurization value.

46. A real-time primary system for electronically tracking received pressurization data, the primary system comprising:

a control syringe capable of generating pressure;

a transducer operably connected to the control syringe, the transducer converting sensed pressure into electrical signals;

a communication link operably connected to the transducer;

a central processing unit;

memory operably coupled to the central processing unit;

a pressurization data input interface operably coupled to the central processing unit and the communication link;

a color graphical display coupled to the central processing unit; and processor means for performing the steps of:
- establishing a plurality of pressurization states including a state of pressurization and a state of depressurization;
- receiving pressurization data that includes pressurization values corresponding to more than one of the plurality of pressurization states;
- changing the background color of the display as the pressurization values transition between any of the plurality of pressurization states; and
- displaying a pressurization arrow indicating whether a current pressurization value represents a state of pressurization or a state of depressurization.

47. A system as recited in claim 46 further comprising processor means for performing the steps of:
- defining a pressurization cycle in terms of the plurality of pressurization states;
- displaying within the pressurization arrow, a count corresponding to a current pressurization cycle;
- defining a zero band of pressurization values;
- displaying a current pressurization value as zero when it falls within the zero band of pressurization values;
- displaying an elapsed time since a last transition between any of the plurality of pressurization states;
- receiving pressurization data that corresponds to a complete pressurization cycle;
- displaying a pressure value corresponding to a maximum pressurization value reached during the complete pressurization cycle;
- displaying a unit of measure corresponding to the displayed pressurization values; and
- displaying an elapsed time of at least one pressurization state that occurred during the complete pressurization cycle.

48. A system as recited in claim 47 further comprising processor means for performing the steps of:
- displaying a two-dimensional grid, the grid having a first axis corresponding to time and a second axis corresponding to magnitude;
- displaying a magnitude indicator on the magnitude axis;
- moving the magnitude indicator to a point on the magnitude axis that corresponds to pressurization values as they are received;
- drawing a point on the grid at the magnitude indicator;
- scrolling the grid away from the magnitude indicator to indicate the passage of time;
- setting a goal corresponding to a desired pressurization value; and
- drawing a line across the grid at the magnitude that corresponds to the pressurization value goal.

49. A system as recited in claim 48 further comprising:

a touch interface integral with the color graphical display; and processor means for performing the steps of:
- receiving a touch input that corresponds to a command for magnifying display of the grid; and
- magnifying display of the grid in a region that is roughly centered about a current pressurization value.

50. A system as recited in claim 49 further comprising processor means for performing the steps of:
- displaying one or more soft keys on the graphical display, one of the soft keys providing the capability of marking current pressurization data to define an event;
- receiving a touch input corresponding to the soft key for marking events; and
- marking the current pressurization data as an event.

51. A system as recited in claim 46 further comprising:

one or more pressure reference standards; and processor means for performing the steps of:
- measuring the one or more pressure reference standards for a first time to produce a first pressure value for each standard;
- storing the first pressure value for each standard;
- measuring each standard subsequent to the first time to produce a subsequent pressure value for each standard;
- comparing the first pressure value and subsequent pressure value for each standard;
- reporting, for each standard, any variation between the first and subsequent pressure values when the variation is greater than a tolerance value.

52. A system as recited in claim 46 further comprising:

a remote system interface;

a remote system that is substantially identical to the primary system; and processor means for performing the steps of:
- establishing a connection between the primary system and the remote system;
- transmitting received pressurization data from the primary system to the remote system;
- synchronizing the displays of the primary and remote systems;
- receiving, from either device, input for controlling how the primary system and remote system operate;
- transmitting any input received at the primary system to the remote system and any input received at the remote system to the primary system; and
- synchronizing the operation of the remote and primary systems when any input is transmitted between the systems.

53. A computer program product for electronically tracking received pressurization data, wherein the pressurization data is received by a real-time primary system that includes a color graphical display, the computer program product comprising:

a computer-readable medium carrying computer-executable instructions comprising:
  program code means for establishing a plurality of pressurization states including a state of pressurization and a state of depressurization;
  program code means for receiving pressurization data that includes pressurization values corresponding to more than one of the plurality of pressurization states;
  program code means for changing the background color of the display as pressurization values transition between any of the plurality of pressurization states; and
  program code means for displaying a pressurization arrow indicating whether a current pressurization value represents a state of pressurization or a state of depressurization.

54. A computer program product as recited in claim 53 wherein the computer-executable instructions further comprising:
  program code means for defining a pressurization cycle in terms of the plurality of pressurization states;
  program code means for displaying within the pressurization arrow, a count corresponding to a current pressurization cycle;
  program code means for defining a zero band of pressurization values;
  program code means for displaying a current pressurization value as zero when it falls within the zero band of pressurization values;
  program code means for displaying an elapsed time since a last transition between any of the plurality of pressurization states;
  program code means for receiving pressurization data that corresponds to a complete pressurization cycle;
  program code means for displaying a pressure value corresponding to a maximum pressurization value reached during the complete pressurization cycle;
  program code means for displaying a unit of measure corresponding to the displayed pressurization values; and
  program code means for displaying an elapsed time of at least one pressurization state that occurred during the complete pressurization cycle.

55. A computer program product as recited in claim 53 wherein the computer-executable instructions further comprise:
  program code means for displaying a two-dimensional grid, the grid having a first axis corresponding to time and a second axis corresponding to magnitude;
  program code means for displaying a magnitude indicator on the magnitude axis;
  program code means for moving the magnitude indicator to a point on the magnitude axis that corresponds to pressurization values as they are received;
  program code means for drawing a point on the grid at the magnitude indicator;
  program code means for scrolling the grid away from the magnitude indicator to indicate the passage of time;
  program code means for setting a goal corresponding to a desired pressurization value; and
  program code means for drawing a line across the grid at the magnitude that corresponds to the pressurization value goal.

56. A computer program product as recited in claim 55 wherein the system includes a touch interface integral with the color graphical display, the computer-executable instructions further comprising:
  program code means for receiving a touch input that corresponds to a command for magnifying display of the grid; and
  program code means for magnifying display of the grid in a region that is roughly centered about a current pressurization value.

57. A computer program product as recited in claim 53 wherein the system includes a touch interface integral with the color graphical display, the computer-executable instructions further comprising:
  program code means for displaying one or more soft keys on the graphical display, one of the soft keys providing the capability of marking current pressurization data to define an event;
  program code means for receiving a touch input corresponding to the soft key for marking events; and
  program code means for marking the current pressurization data as an event.

58. A computer program product as recited in claim 53 wherein the system includes one or more pressure reference standards, the computer-executable instructions further comprising:
  program code means for measuring the one or more pressure reference standards for a first time to produce a first pressure value for each standard;
  program code means for storing the first pressure value for each standard;
  program code means for measuring each standard subsequent to the first time to produce a subsequent pressure value for each standard;
  program code means for comparing the first pressure value and subsequent pressure value for each standard;
  program code means for reporting, for each standard, any variation between the first and subsequent pressure values when the variation is greater than a tolerance value.

59. A computer program product as recited in claim 53 wherein the system includes a remote system interface and a remote system that is substantially identical to the primary system, the computer-executable instructions further comprising:
  program code means for establishing a connection between the primary system and the remote system;
  program code means for transmitting received pressurization data from the primary system to the remote system;
  program code means for synchronizing the displays of the primary and remote systems;
  program code means for receiving, from either device, input for controlling how the primary system and remote system operate;
  program code means for transmitting any input received at the primary system to the remote system and any input received at the remote system to the primary system; and
  program code means for synchronizing the operation of the remote and primary systems when any input is transmitted between the systems.

60. A computer program product as recited in claim 54 wherein the primary system includes a touch interface and is capable of tracking pressurization values in at least two units of measure, the units of measure arranged in a circular sequence, the computer executable instructions further comprising:

program code means for receiving a touch input corresponding to the display of a unit of measure;

program code means for displaying the unit of measure that is next in the circular sequence; and program code means for updating the display of pressurization values to reflect the displayed unit of measure.

61. A computer program product as recited in claim 53 wherein the primary system includes memory, the computer-executable instructions further comprising:

program code means for dividing pressurization data into one or more discrete events; and program code means for storing the one or more discrete events in the memory.

\* \* \* \* \*

UNITED STATES PATENT AND TRADEMARK OFFICE
CERTIFICATE OF CORRECTION

PATENT NO.   : 6,533,757 B1                                                Page 1 of 1
DATED        : March 18, 2003
INVENTOR(S)  : Fred P. Lampropoulos et al.

It is certified that error appears in the above-identified patent and that said Letters Patent is hereby corrected as shown below:

Column 6,
Line 67, change "11described" to -- described --

Column 7,
Line 65, change "Espafiol" to -- Español --

Column 15,
Lines 20-21, change "U.S. letters patent" to -- United States Letters Patent --

Column 20,
Line 6, before "the" insert -- to --

Column 27,
Line 3, change "computer executable" to -- computer-executable --

Signed and Sealed this

Thirteenth Day of April, 2004

JON W. DUDAS
*Acting Director of the United States Patent and Trademark Office*